(12) United States Patent
Fleming, III (10) Patent No.: US 8,252,019 B2
(45) Date of Patent: Aug. 28, 2012

(54) FILTER RETRIEVAL CATHETER SYSTEM, AND METHODS

(75) Inventor: James A. Fleming, III, Bethlehem, PA (US)

(73) Assignee: Cordis Corporation, Bridgewater, NJ (US)

( * ) Notice: Subject to any disclaimer, the term of this patent is extended or adjusted under 35 U.S.C. 154(b) by 589 days.

(21) Appl. No.: 12/290,612

(22) Filed: Oct. 31, 2008

(65) Prior Publication Data

US 2009/0099574 A1   Apr. 16, 2009

Related U.S. Application Data

(63) Continuation-in-part of application No. 10/540,778, filed on Mar. 3, 2006, now abandoned.

(51) Int. Cl.
*A61M 29/00* (2006.01)
(52) U.S. Cl. ........................... 606/200; 606/113
(58) Field of Classification Search ............ 606/45, 606/47, 108, 110, 113, 114, 127, 139, 148, 606/159, 191, 200; 623/1.11, 1.23, 2.11
See application file for complete search history.

(56) References Cited

U.S. PATENT DOCUMENTS

| | | | | |
|---|---|---|---|---|
| 1,833,687 A | * | 11/1931 | Neivert | 606/113 |
| 4,718,419 A | * | 1/1988 | Okada | 606/47 |
| 5,171,314 A | * | 12/1992 | Dulebohn | 606/113 |
| 5,211,650 A | * | 5/1993 | Noda | 606/139 |
| 5,224,488 A | * | 7/1993 | Neuffer | 600/564 |
| 5,300,078 A | * | 4/1994 | Buelna | 606/113 |
| 5,342,371 A | * | 8/1994 | Welter et al. | 606/113 |
| 5,387,219 A | * | 2/1995 | Rappe | 606/108 |
| 5,554,163 A | * | 9/1996 | Shturman | 606/159 |
| 5,795,322 A | | 8/1998 | Boudewijn | |
| 5,810,874 A | | 9/1998 | Lefebvre | |
| 5,895,399 A | | 4/1999 | Barbut et al. | |
| 5,911,725 A | * | 6/1999 | Boury | 606/108 |
| 5,989,264 A | * | 11/1999 | Wright | 606/113 |
| 6,099,549 A | | 8/2000 | Bosma et al. | |

(Continued)

FOREIGN PATENT DOCUMENTS

WO   WO 00/16846   3/2000

(Continued)

OTHER PUBLICATIONS

European Search Report, issued by the European Patent Office for related European Appln No. 04706990, dated Mar. 15, 2007.

*Primary Examiner* — Corrine M McDermott
*Assistant Examiner* — Steven Ou (57) ABSTRACT

A filter retrieval system for retrieving a previously implanted medical filter, and methods of using the retrieval system, are disclosed. The filter retrieval system has a flexible shaft, a retrieval element, and a handle with an actuator. The flexible shaft may be catheter-based, and has a proximal and a distal end, and has an opening near its distal end. The handle is affixed to the shaft near the proximal end of the shaft, and the actuator is adapted to manipulate the retrieval element. When an operator manipulates the actuator, the retrieval element is adapted to protrude slightly from the shaft opening. As the actuator is operated, the retrieval element can grasp or hook or otherwise engage a portion of the filter, and then pull the filter in through the opening into a passage or lumen of the catheter shaft. The retrieval system is capable of retrieving a filter in into a proximal and distal space defined by the flexible shaft, though only one space at a time.

4 Claims, 13 Drawing Sheets

U.S. PATENT DOCUMENTS

| | | |
|---|---|---|
| 6,224,612 B1 * | 5/2001 | Bates et al. .................. 606/114 |
| 6,245,087 B1 | 6/2001 | Addis |
| 6,342,062 B1 * | 1/2002 | Suon et al. .................. 606/200 |
| 6,443,972 B1 | 9/2002 | Bosma et al. |
| 6,485,501 B1 | 11/2002 | Green |
| 6,517,550 B1 * | 2/2003 | Konya et al. ................ 606/113 |
| 6,540,765 B1 | 4/2003 | Malacoff |
| 6,596,011 B2 | 7/2003 | Johnson et al. |
| 6,958,074 B2 | 10/2005 | Russell |
| 6,989,021 B2 | 1/2006 | Bosma et al. |
| 7,101,378 B2 * | 9/2006 | Salameh et al. ............. 606/113 |
| 7,691,111 B2 * | 4/2010 | Bates et al. .................. 606/114 |
| 7,753,917 B2 * | 7/2010 | Urbanski et al. ............ 606/108 |
| 7,824,342 B2 * | 11/2010 | Minosawa et al. ........... 600/564 |
| 2002/0045918 A1 * | 4/2002 | Suon et al. .................. 606/200 |
| 2002/0188262 A1 * | 12/2002 | Abe ............................. 604/326 |
| 2003/0135222 A1 * | 7/2003 | Baska .......................... 606/113 |
| 2004/0092953 A1 * | 5/2004 | Salameh et al. ............. 606/113 |
| 2005/0119668 A1 * | 6/2005 | Teague et al. ................ 606/127 |
| 2006/0190007 A1 * | 8/2006 | Bates et al. .................. 606/113 |
| 2009/0112244 A1 * | 4/2009 | Freudenthal ................. 606/167 |

FOREIGN PATENT DOCUMENTS

| | | |
|---|---|---|
| WO | WO 01/56484 | 8/2001 |
| WO | WO 02/11626 | 2/2002 |

* cited by examiner

FILTER RETRIEVAL CATHETER SYSTEM, AND METHODS

CROSS-REFERENCE TO RELATED APPLICATION

This application claims priority of U.S. Provisional Patent Application No. 60/444,320 filed Jan. 31, 2003. This application is a continuation-in-part of U.S. patent application Ser. No. 10/540,778 filed Mar. 3, 2006 now abandoned.

BACKGROUND OF THE INVENTION

1. Technical Background

The present invention generally relates to a catheter system to retrieve a filter which has been previously implanted in a body passage for medical treatment of a patient.

2. Discussion

Many different types of filters may be implanted in various body passages for medical treatment of a patient. The present invention will be described by using the specific example of a vascular filter for implantation in a blood vessel, and an example of one particular type of filter retrieval system for retrieving a vascular filter. However, it should be understood that the present invention is not limited to vascular applications, but rather relates to implantable filters for use in any medically suitable type of body passage, for example, the vascular system, biliary system or pulmonary system, esophagus, etc.

Implantable filters may be of various types and designs, including for example permanent or retrievable; they may be made of various types of materials, such as metals and/or polymers; and they may have any of numerous designs. Some implantable filters are resilient, having some degree of "spring" characteristics. This resilience may be present for example along a longitudinal axis of the filter, and/or for example may allow resilient bending along one or more axes of the filter, and/or for example may allow resilient compression of the filter. This latter type of "compressible" filter may be delivered to a desired site for treatment through a catheter system having a passage or lumen containing the filter. When the filter is released from the catheter, it thus tends to resilient expand to a larger size suitable for the size of the body passage at the desired site for treatment.

Permanent filters are not intended for removal, and retrievable filters are intended to be removable for a period of time after being implanted. In other words, a physician has a period of time in which to choose whether to remove a retrievable filter or not. In the specific case of a vascular filter, it may be desirable to have the option to retrieve a filter, for example a filter that has been placed in the inferior vena cava. It may also be desirable to retrieve such vascular filters with a catheter-based retrieval system, from an access point into an artery, for example. Such a catheter-based retrieval system enables the physician to retrieve the filter percutaneously, without performing surgery. In some situations, the desired access point may be into the jugular artery or the femoral artery.

Regarding the filter itself, it may be desirable to provide a medical implantable filter with features(s) for resisting movement of the filter within the body passageway. These features for resisting movement of the filter may be for example one or more resilient anchors, hooks, or barbs, etc. Such movement resistors may be one-directional, resisting displacement in one direction and allowing for removal of the filter in the other direction.

BACKGROUND OF THE INVENTION

In the example of a vascular filter, the filter may be designed to resist movement from the desired site for treatment in a cranial direction, defined as being opposite a caudal direction. These types of filters are often resilient, and can be radially compressed into a smaller size, and may be removed by a catheter system that is inserted into the femoral artery, has a hook or loop member that passes through a passage or lumen through the catheter which catches the filter, and pulls the filter into the catheter lumen in the caudal direction. The catheter system and captured filter may then be removed from the patient.

It may also be desirable to remove a filter in the cranial direction, by introducing a catheter retrieval system through the jugular artery or brachial artery, and approaching the filter from the cranial direction. However, this approach may not be desirable, if the particular filter is designed to resist movement in the cranial direction.

The retrieval system of the present invention is capable of retrieving a filter when approaching from either direction. In other words, the present catheter-based retrieval system can be inserted through the femoral artery and approach the filter from the caudal direction to retrieve the filter, or through the jugular or brachial artery and approach the filter from the cranial direction, to retrieve the filter. This versatility is provided for approaching the filter from either direction, but enables the movement of the filter during retrieval to be in either direction. Accordingly, the filter can be pulled in the direction of movement that the filter does not resist, regardless of the direction from which the catheter-based retrieval system approaches the filter.

One example of a retrieval catheter system according to the present invention thus allows a filter to be designed to resist movement in the cranial direction, while still permitting retrieval by approaching the filter with a catheter-based retrieval system from either the cranial direction or the caudal direction.

In operation of a vascular filter retrieval system, the system may provide for "pulling" the filter a slight distance in the caudal direction to retract the filter anchors or barbs from engagement with the vessel, before "capturing" the filter within the catheter system, and then retrieving the catheter system and captured filter from whichever access point was selected, and thus in whichever direction is desired. This flexibility of approach may provide greater therapeutic options for treatment of patients.

Accordingly, a general possible object of the present invention is to provide filter retrieval systems for retrieving a previously implanted medical filter, and methods for using the retrieval systems.

Another possible object of this invention is to provide an improved filter retrieval system capable of retrieving a filter in either a proximal or a distal direction, as may be preferred by a physician.

These and other possible objects, features and advantages of the present invention will be apparent from and clearly understood through a consideration of the following detailed description of the preferred embodiment.

Many catheter systems are used with a flexible guidewire. The guidewire is often metal, and is slidably inserted along the desired body passage. The catheter system is then advanced over the guidewire by "back-loading" or inserting the proximal end of the guidewire into a distal guidewire port leading to a guidewire lumen defined by the catheter system. Such a guidewire lumen may extend along the entire length or only part of the catheter.

It is desirable to provide a balloon catheter having an optimum combination of various performance characteristics, which may be selected among: flexibility, lubricity, pushability, trackability, crossability, low profile, pull strength, inflation/deflation times, inflation pressures, and others. Flexibility may relate to bending stiffness of a medical device (balloon catheter and/or stent, for example) in a particular region or over its entire length, or may relate to the material hardness of the components. Lubricity may refer to reducing friction by using low-friction materials or coatings. Pushability may relate to the column strength of a device or system along a selected path. Trackability may refer to a capability of a device to successfully follow a desired path, for example without prolapse. Crossability may be clarified by understanding that physicians prefer to reach the desired site with the balloon catheter while encountering little or no friction or resistance. Profile may refer to a maximum lateral dimension of the balloon catheter, at any point along its length.

The balloon catheter of the present invention provides various advantages, which may include: pushability, optimized flexibility along the catheter length, torsional strength, pull strength, low profile, etc. Some embodiments of the present invention may also provide additional benefits, including smooth transitions in flexibility, lubricious guidewire lumen, etc.

Structurally, catheters may have a flexible shaft extending between a proximal end and a distal end, and define one or more tubular passages or "lumens" extending through part or all of the catheter shaft. Such lumens often have one or more openings, referred to as "ports."

When a lumen is adapted to slidingly receive a guidewire, it is referred to as a "guidewire lumen," and it will generally have a proximal and distal "guidewire port." The distal guidewire port is often at or near the catheter shaft distal end.

A hub is often affixed to the catheter shaft proximal end. The hub may serve a variety of functions, including providing a handle for manipulating the catheter, and/or defining proximal port(s) communicating with lumen(s) defined by the catheter shaft. When the catheter has a guidewire lumen, a proximal guidewire port may be located at some point along the sidewall of the catheter shaft, or a hub may define the proximal guidewire port.

A guidewire has a flexible wire-like structure extending from a proximal end to a distal end. The guidewire will usually be of a size selected to fit into and slide within a corresponding guidewire lumen of a catheter.

The terms "tube" and "tubular" are used in their broadest sense, to encompass any structure arranged at a radial distance around a longitudinal axis. Accordingly, the terms "tube" and "tubular" include any structure that (i) is cylindrical or not, such as for example an elliptical or polygonal cross-section, or any other regular or irregular cross-section; (ii) has a different or changing cross-section along its length; (iii) is arranged around a straight, curving, bent or discontinuous longitudinal axis; (iv) has an imperforate surface, or a periodic or other perforate, irregular or gapped surface or cross-section; (v) is spaced uniformly or irregularly, including being spaced varying radial distances from the longitudinal axis; or (vi) has any desired combination of length or cross-sectional size.

Any suitable additional material may also be used to make catheters and hubs as described, including polymers and other materials suitable for use with medical devices.

It is of course possible to build various kinds and designs of catheters according to the present invention, by various techniques and of various materials, to obtain the desired features. It should be noted that the present invention also relates to methods for making and using medical devices, during or in preparation for medical treatment of a patient.

These and various other objects, advantages and features of the invention will become apparent from the following description and claims, when considered in conjunction with the appended drawings. The invention will be explained in greater detail below with reference to the attached drawings of a number of examples of embodiments of the present invention.

BRIEF DESCRIPTION OF THE DRAWINGS

In the course of this description of preferred embodiments, reference will be made to the attached drawings, wherein.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

One possible arrangement of a filter retrieval system of the present invention is shown in the drawings. Filter retrieval system 10 includes a shaft 12, a retrieval element 14, and a handle 16 with an actuator 18. Retrieval element 14 may be a loop as shown, or may be a snare, hook or any other desired shape or type of retrieval device.

The shaft 12 may be catheter-based, and has a proximal and a distal end 20 and 22. The shaft 12 has an opening 24 in its sidewall 26 positioned a distance from the shaft distal end 22. In addition, the shaft 12 may define a lumen or passage 28 from its proximal end 20 to its distal end 22, or at least near its distal end 22. The shaft preferably has an optimum selection of characteristics, including flexibility, column strength or pushability, torque transmission, steerability, etc.

A first and second internal space 30 and 32 are defined inside the shaft 12, located immediately proximal and distal from the side opening 24. The opening 24 or sidehole or slot is preferably spaced from the distal end 22 of the catheter shaft 12 a distance longer or slightly longer than the length of the filter to be retrieved, so that the first and second internal spaces 30 and 32 are sufficiently large to hold the filter inside one of them after the filter has been captured.

The handle 16 is affixed to the shaft 12 near the proximal end 20 of the shaft 12, has an interface for an actuator 18, and provides a comfortable way to manipulate, steer, and direct the retrieval system 10. The actuator 18 is adapted to manipulate the retrieval element 14 by selectively moving the retrieval element 14 in proximal and/or distal directions. The particular actuator 18 shown in the drawings is a wheel having an axle 34 and 36 extending from each side of the wheel. The wheel may have finger ridges as shown.

The actuator 18 should be coupled with the retrieval element 14, so that moving forces applied to the actuator 18 will be transmitted to the retrieval element 14, and move it in a corresponding fashion. The particular construction for transmitting such forces shown in the drawings is a main fiber or wire loop 38, extending from a first and second end 40 and 42 of the main wire loop 38, wound around each of the axles 34 and 36 in opposing directions, through a lumen 28 defined by the shaft 12 to a position near the distal end 22 of the shaft 12, where the main wire loop 38 has a 180-degree bend.

A pin 44, or pulley or bent tube or 180-degree lumen or any other suitable guide is provided, causing the main wire loop 38 to move around it. The guide may be provided if the material of the main fiber or wire loop 38 has no substantial column strength, or cannot transmit an effective pushing force from the proximal handle 16 and actuator 18 to the retrieval element 14. This loop 38 (and/or the retrieval element 14) may be formed of a wide variety of materials, including organic fibers, polymers, and even some metals.

The main wire loop 38 is affixed to the retrieval element 14, so that rotation of the wheel 18 in one direction causes the retrieval element 14 to move in the proximal direction, while rotation of the wheel 18 in the opposite direction causes the retrieval element 14 to move in the distal direction.

The handle 16 and actuator 18 may of course have any preferred design or shape suitable for accomplishing their desired functions. For example, the handle may have a more ergonomic shape, or the actuator may be shaped like a lever, or a slider, etc. The retrieval element may have any shape suitable for grasping, snaring, snagging or catching a corresponding retrieval feature on whatever type of filter is to be retrieved. The filter shown in FIGS. 6A-6I and 7A-7J is one example of numerous filter designs that the filter retrieval systems of the present invention can retrieve. The particular filter 46 depicted in the drawings has a retrieval feature 48 in the form of a hook at one end, and a series of anchors or barbs 50 for resisting movement of the filter 46 within a body passage (which is not shown for clarity purposes).

Figures 8, 9:
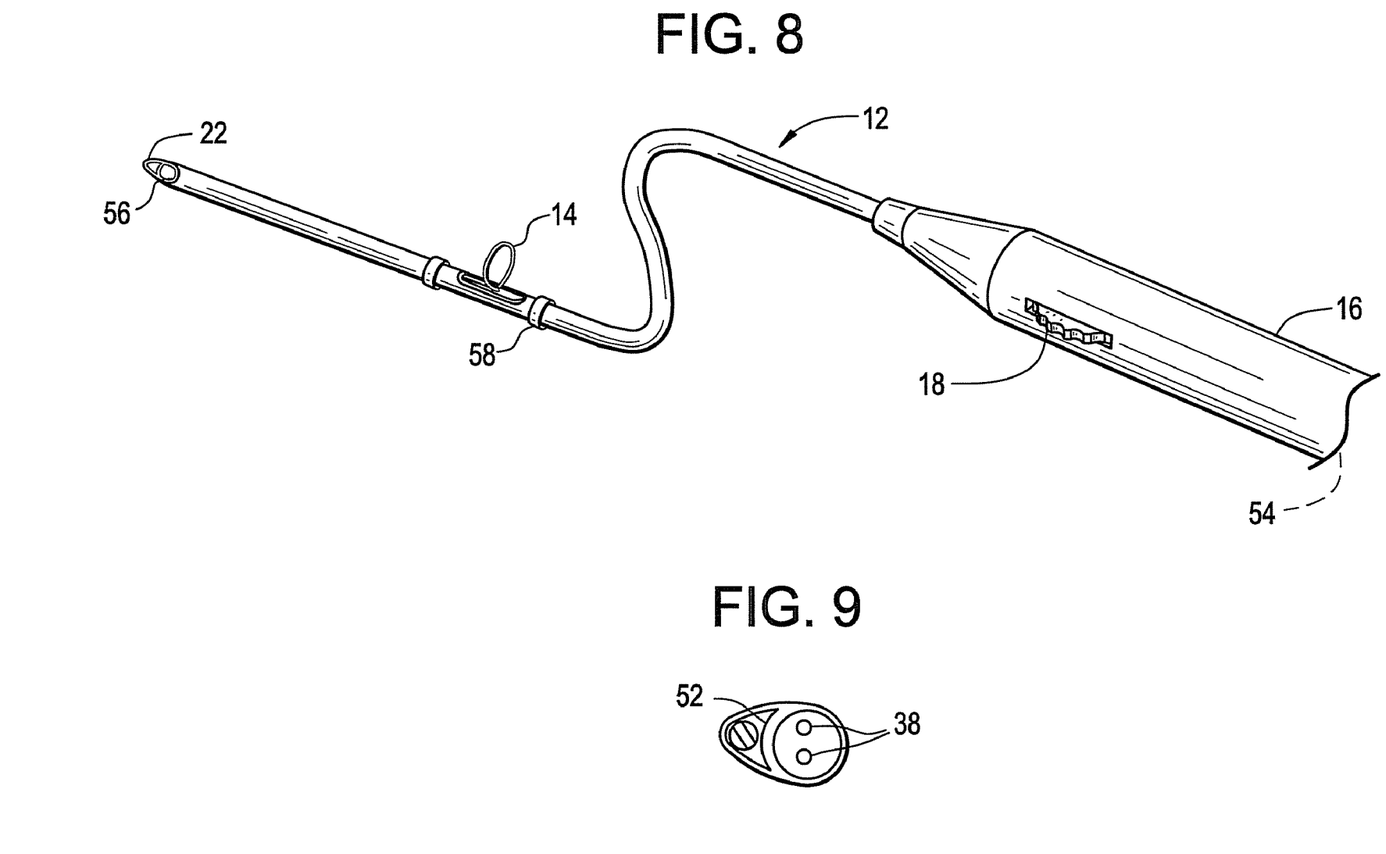
FIG. 8 is a perspective view of a catheter-based filter retrieval system, showing the catheter shaft following a curved path.
FIG. 9 is a transverse cross-sectional view of a catheter-based filter retrieval system, showing a guidewire lumen.

FIGS. 8 and 9 show possible features of the retrieval system, including the catheter shaft following a curved path, a guidewire lumen 52 having a proximal and distal guidewire port 54 and 56, and one or more marker bands 58.

In operation generally, the retrieval system may inserted into a body passage such as an artery through a percutaneous access point. For example, the access point may be into the femoral, jugular, or brachial arteries. The retrieval system is advanced until the side opening in the shaft is positioned near a desired point on a previously implanted filter. In an initial configuration, the retrieval element is inside the shaft. When the system is suitably positioned, the physician may manipulate the actuator, so that the retrieval element is moved to protrude from the shaft opening. As the actuator is further operated, the retrieval element can grasp or hook or otherwise engage a portion of the filter, and then pull the filter in through the opening into one of the internal spaces of the catheter shaft. The captured filter and the retrieval system may then be removed from the patient. The retrieval system may be capable of retrieving a filter in either a proximal or a distal direction as desired.

In particular, when the catheter system is advanced to position the catheter sidehole and snare near a corresponding retrieval element on the filter, the snare is hooked or attached to the filter retrieval element by manipulating the catheter and spool. Once the snare grabs the filter retrieval element, which may be a hook, loop, catch, barb, etc., the snare and filter may be pulled in through the catheter sidehole in either a proximal or a distal direction depending upon the orientation of the catheter to the filter. The catheter and the captured filter may then be removed from the patient.

Figure 1:
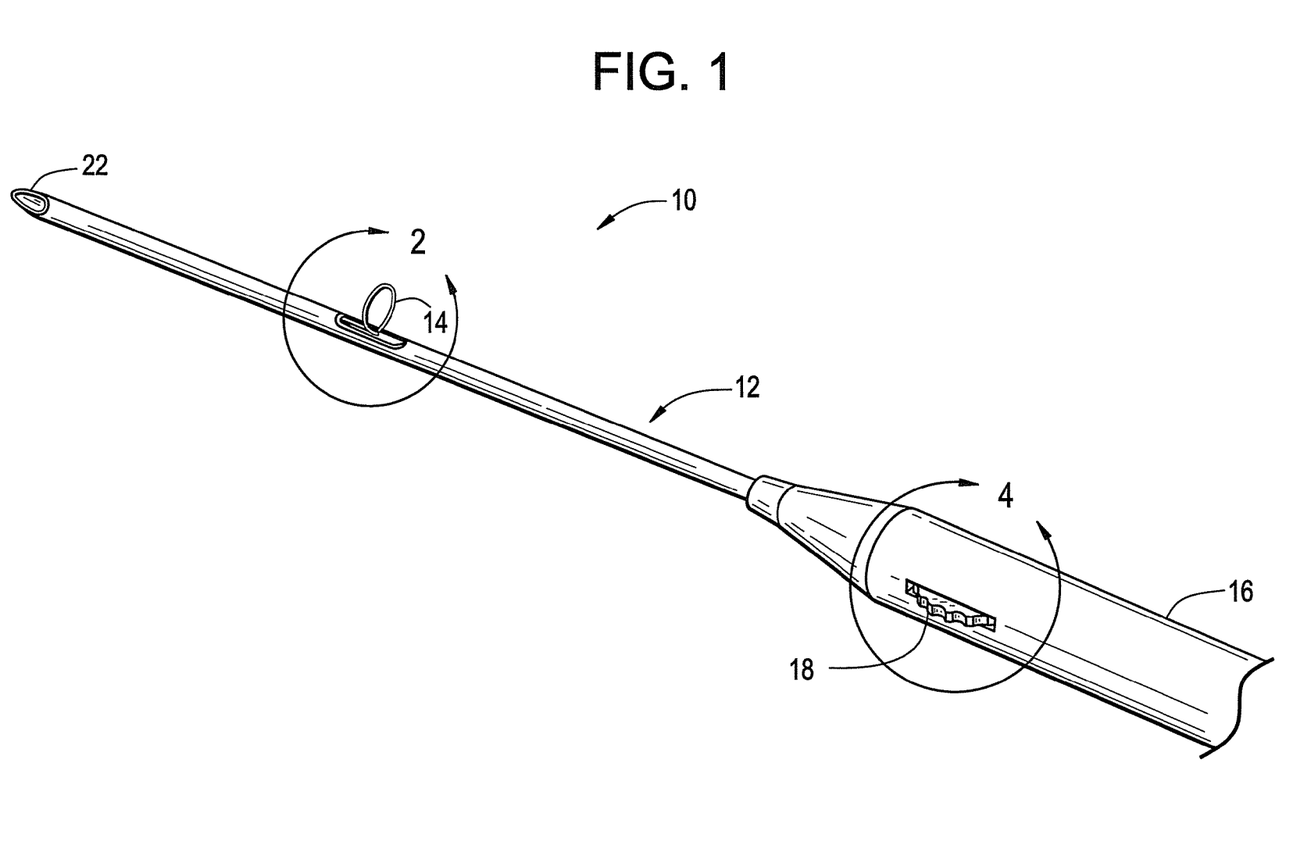
FIG. 1 is a perspective view of a catheter-based filter retrieval system, arranged according to the principles of the present invention.
Figure 2:
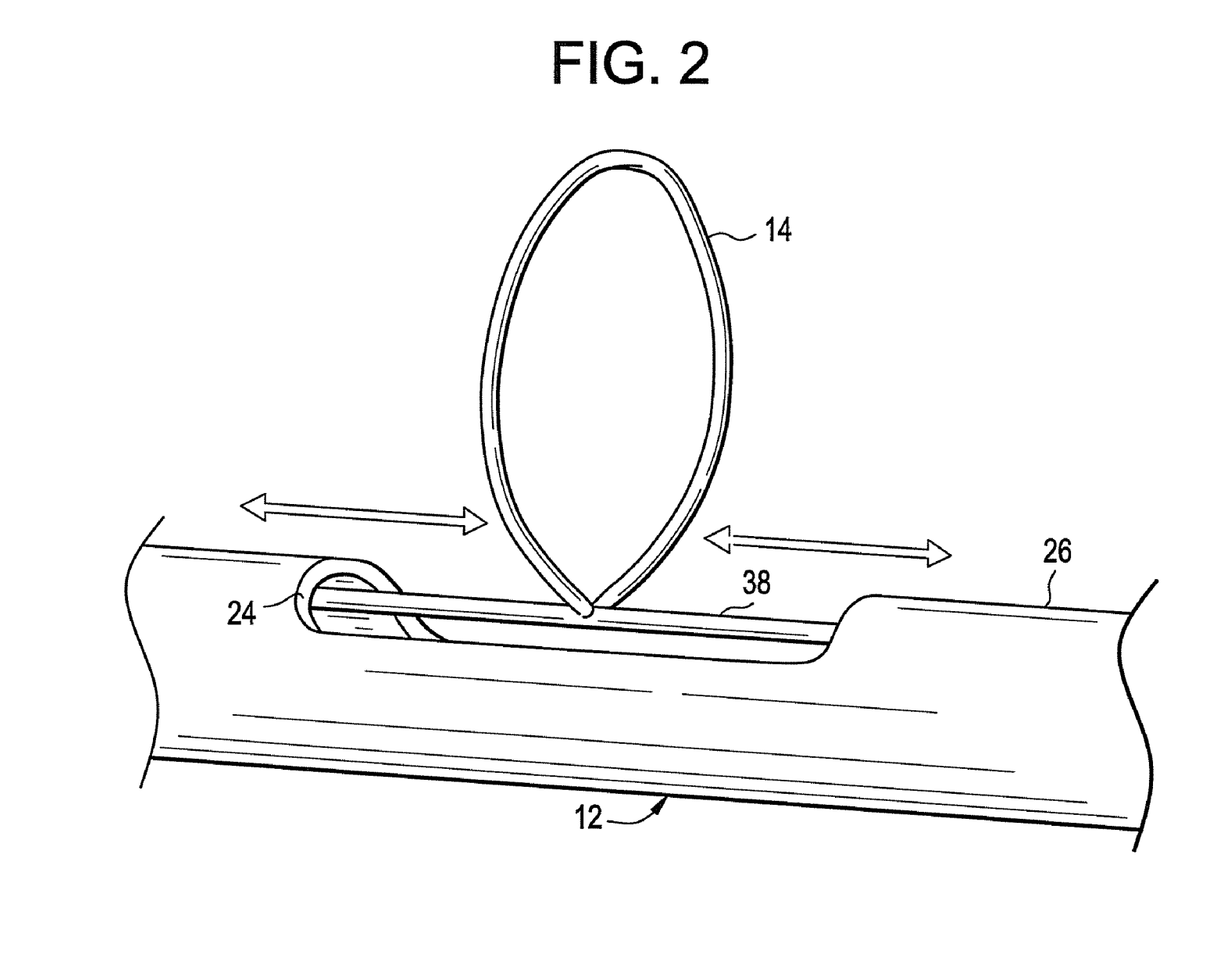
FIG. 2 is a partial perspective view of a portion of the filter retrieval system of FIG. 1, including a shaft opening and snare loop.
Figure 3:
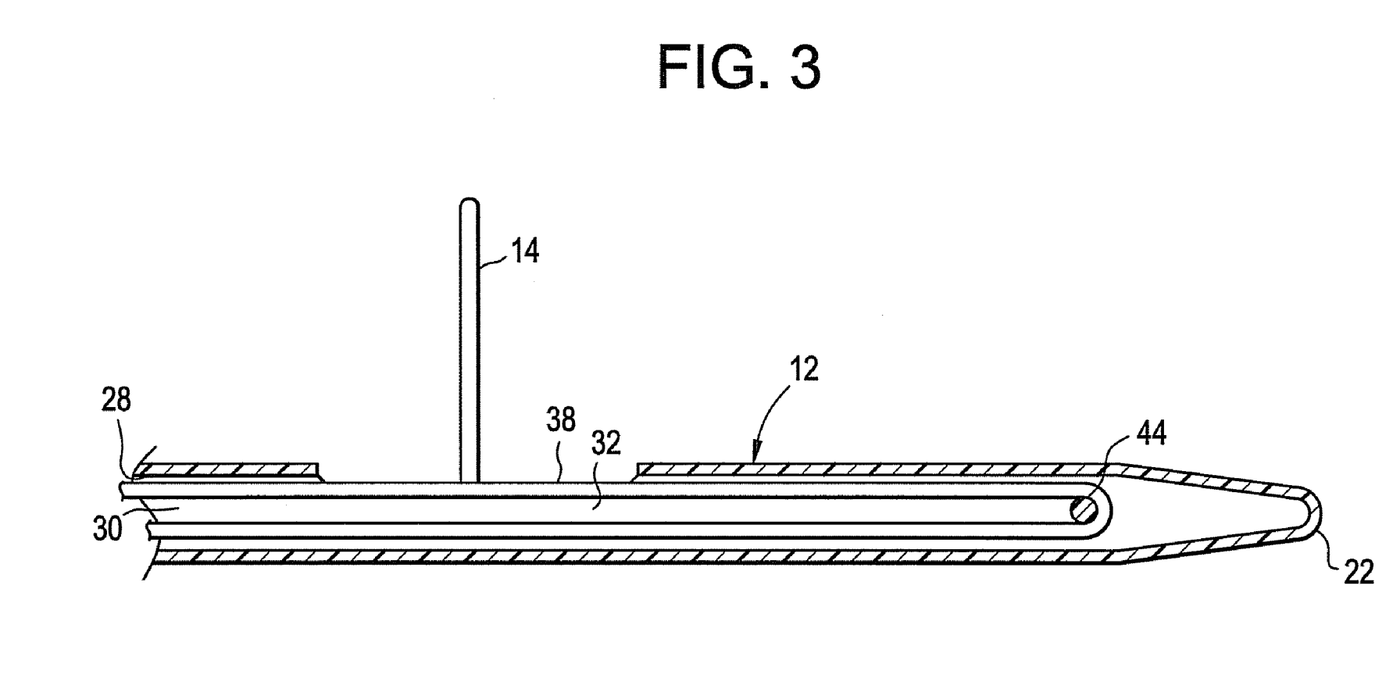
FIG. 3 is a partial cross-section view of the distal end of the filter retrieval system of FIG. 1.
Figure 4:
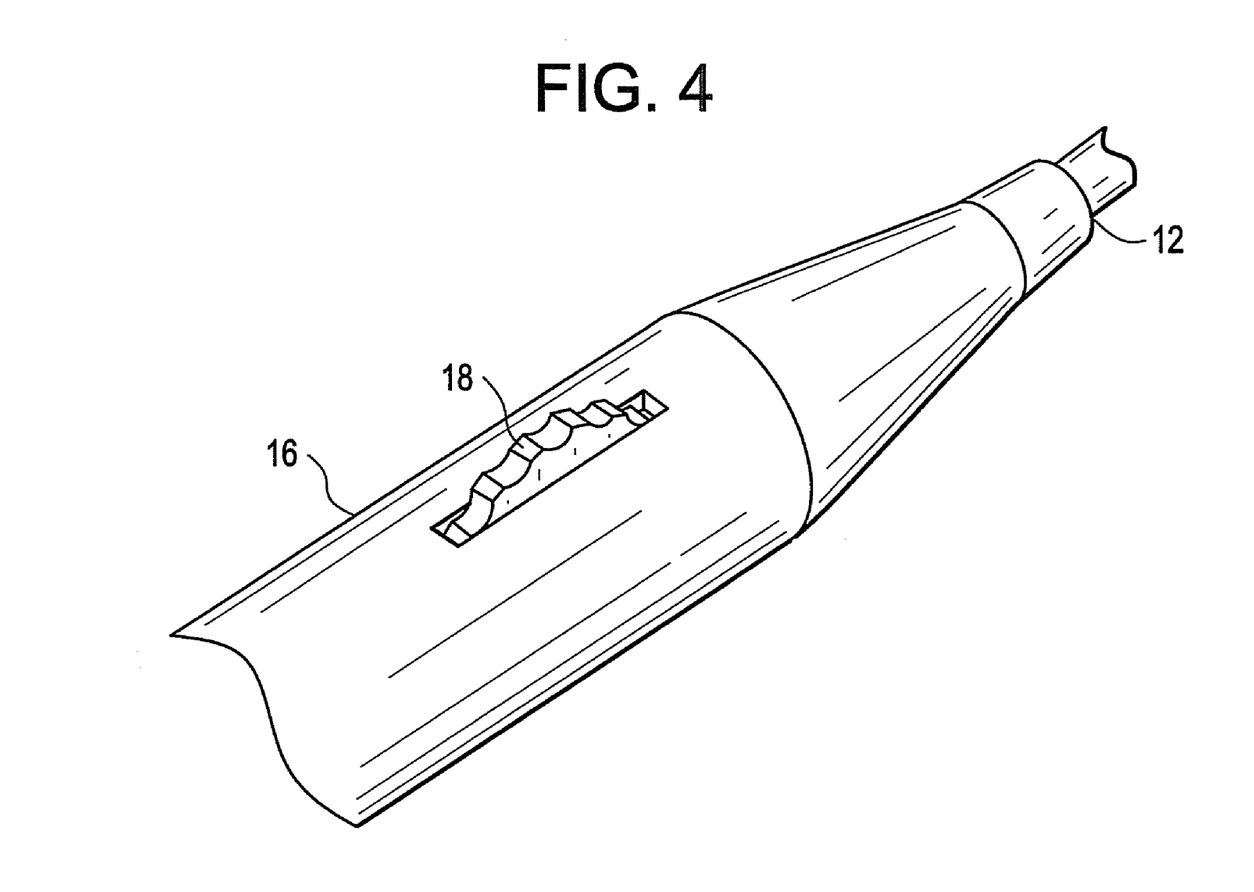
FIG. 4 is a partial perspective view of some components of the filter retrieval system of FIG. 1, including a handle and actuator wheel.
Figure 5:
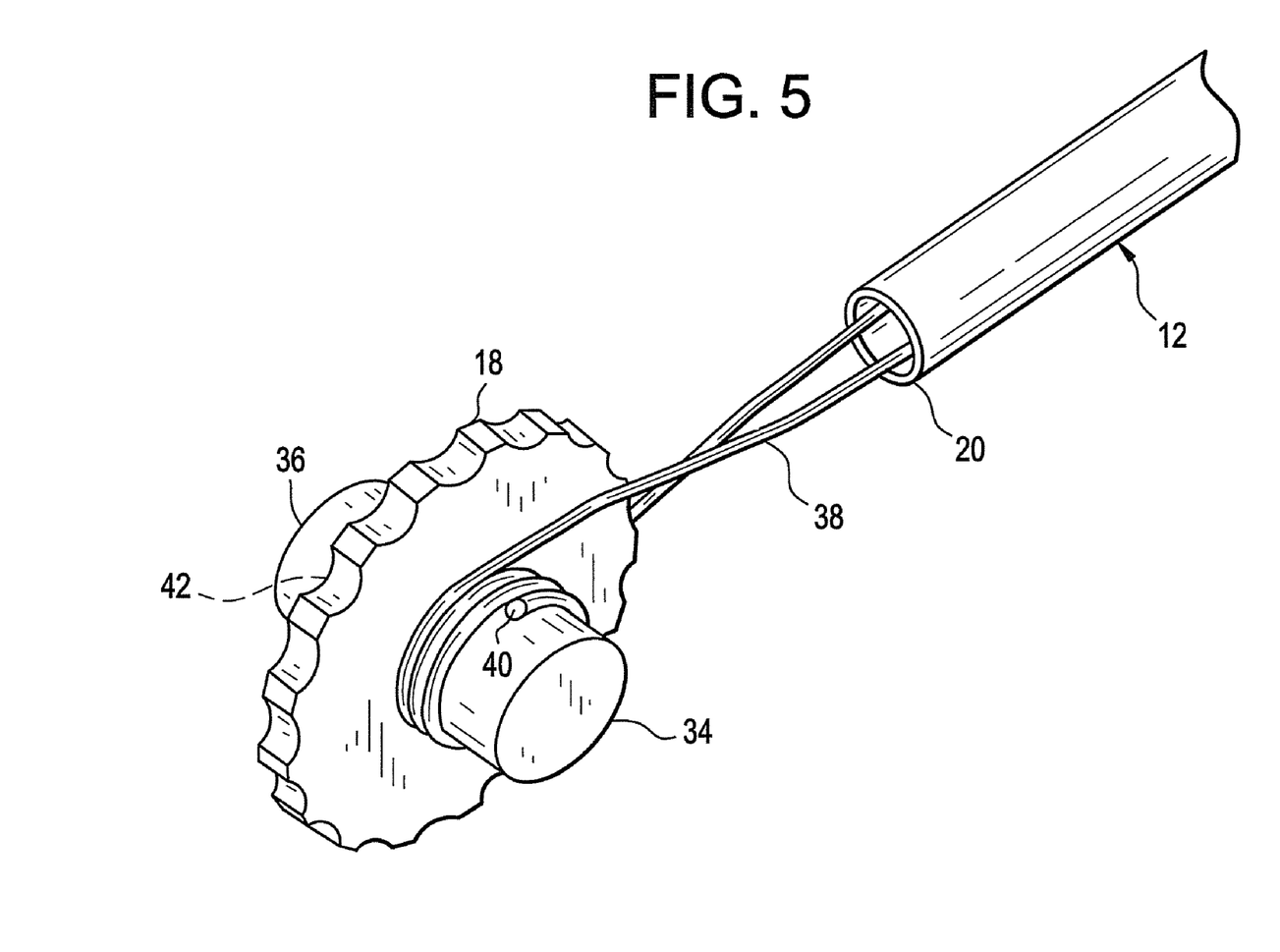
FIG. 5 is a partial perspective view of some components of the filter retrieval system of FIG. 1, including an actuator wheel, wire, and shaft tube.
Figure 6A:
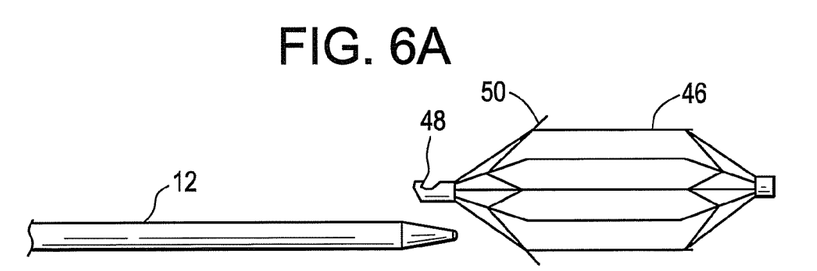
FIGS. 6A-6I illustrate a first method of using the system of FIG. 1 to retrieve a previously implanted filter in a proximal direction.
Figure 6B:
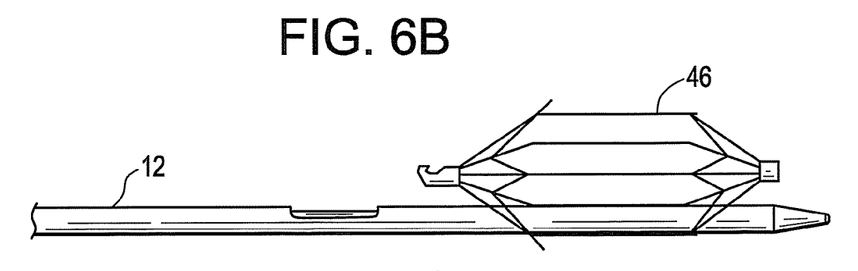

To retrieve a filter in the proximal direction, as shown in FIGS. 6A-6B, the distal end 22 of the shaft 12 is advanced to a position near the filter 46 until the sidehole 24 is aligned with the filter retrieval feature 48, which may be for example one or more hooks, barbs, loops, etc.

Figure 6C:
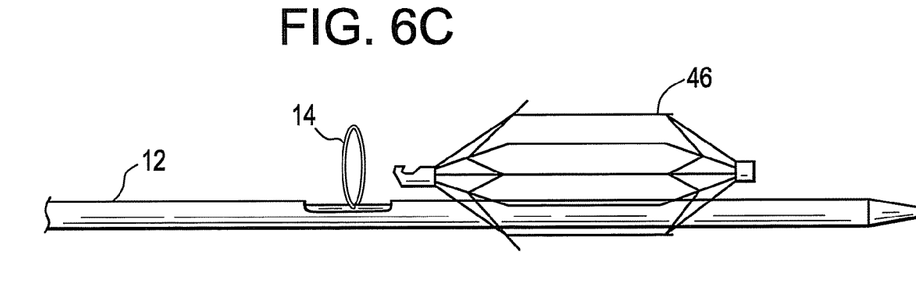

The wheel 18 is rotated slightly to move the main wire loop 38 inside the catheter shaft 12 to expose the retrieval element or snare 14, shown in FIG. 6C.

Figure 6D:
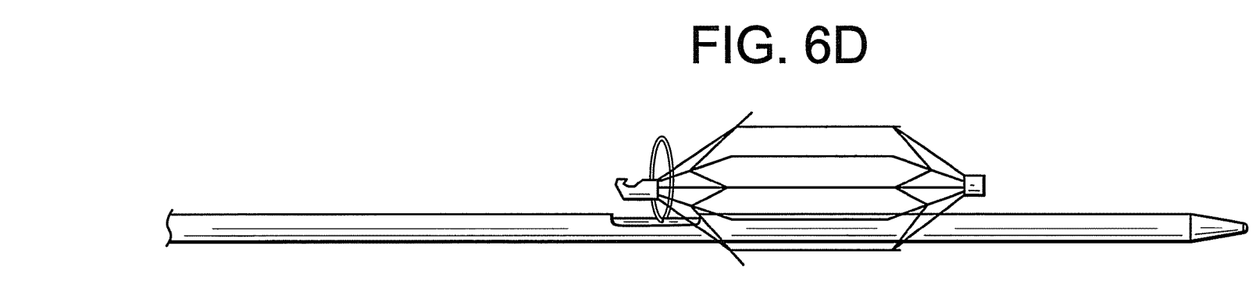
Figure 6E:
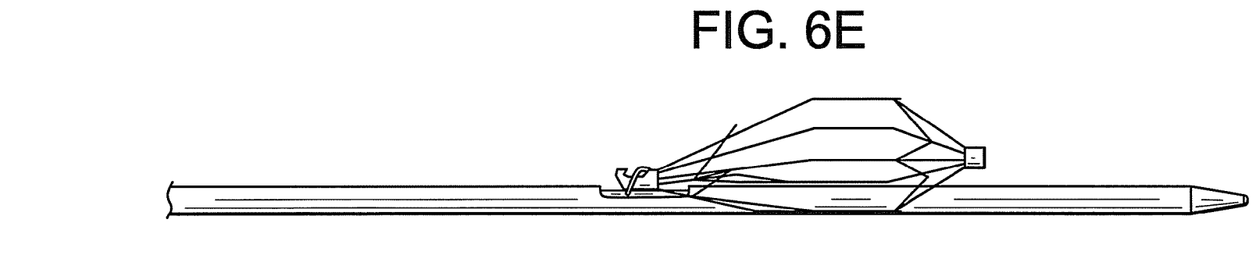
Figure 6F:
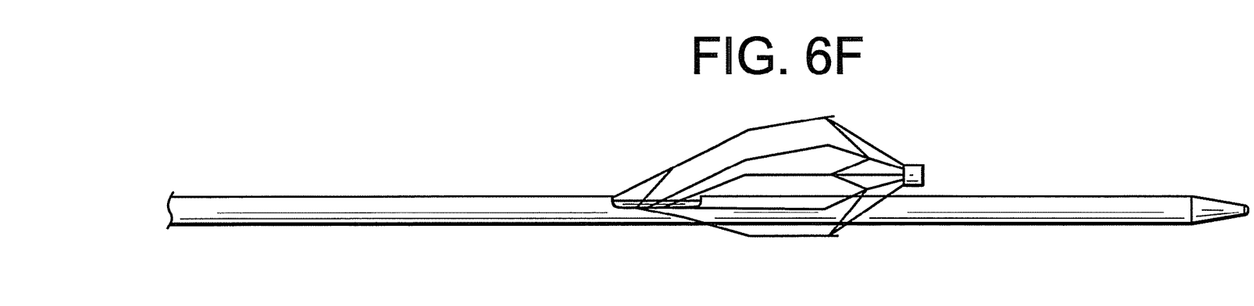
Figure 6G:
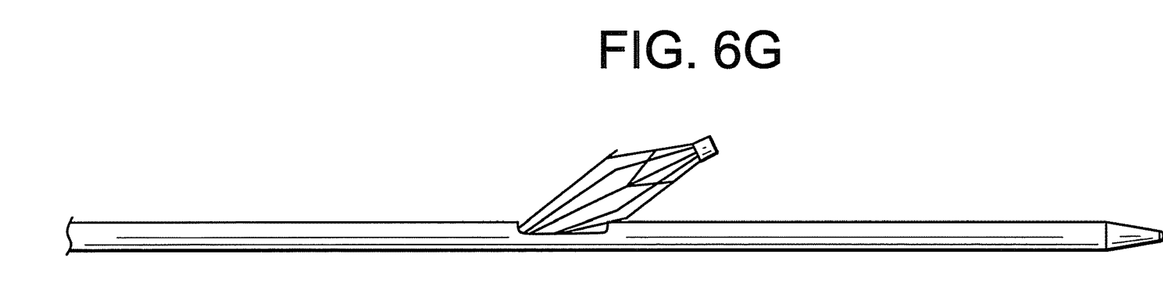
Figure 6H:
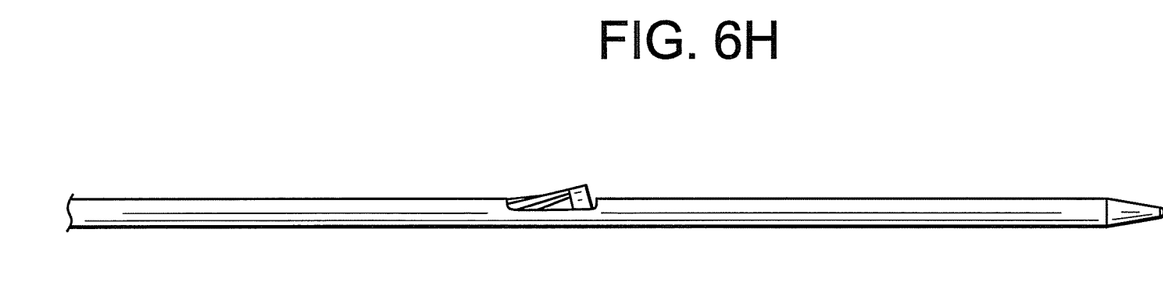
Figure 6I:
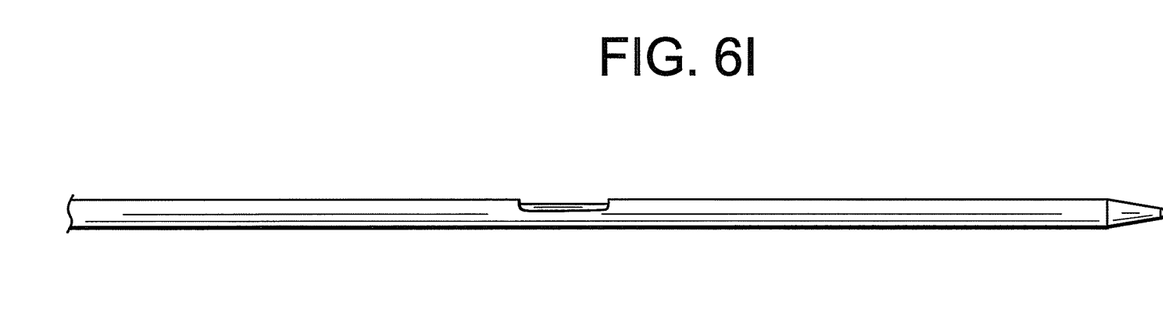

The catheter shaft is pushed or advanced toward the filter so that the snare 14 is advanced over the filter retrieval feature 48 or attachment point, shown in FIG. 6D.

The wheel 18 is again rotated to pull the main wire loop 38 inside the catheter shaft 12 in the proximal direction, to draw the filter 46 into the catheter shaft 12 until it is inside the proximal internal space 30, shown in FIGS. 6E-6I. The retrieval system and captured filter are then removed from the body.

Figure 7A:
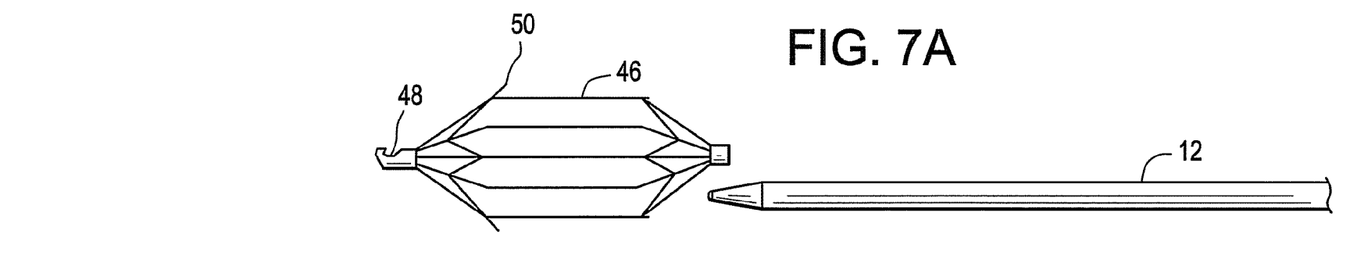
FIGS. 7A-7J illustrate a second method of using the system of FIG. 1 to retrieve a previous implanted filter in a distal direction.
Figure 7B:
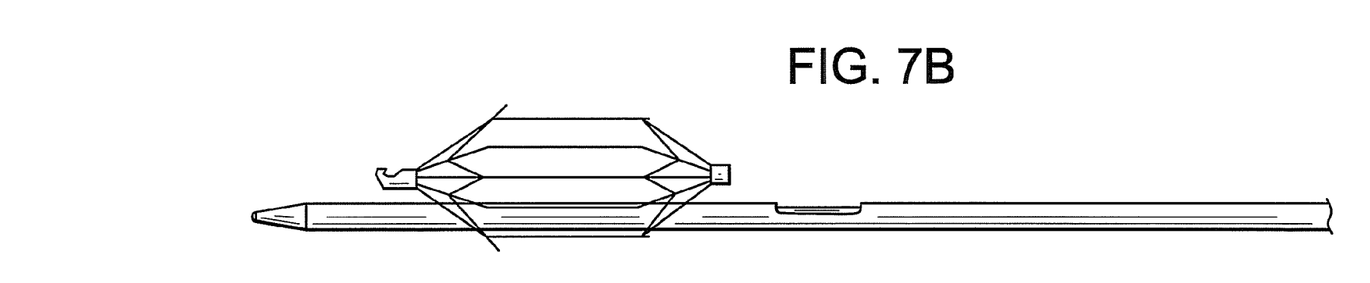
Figure 7C:
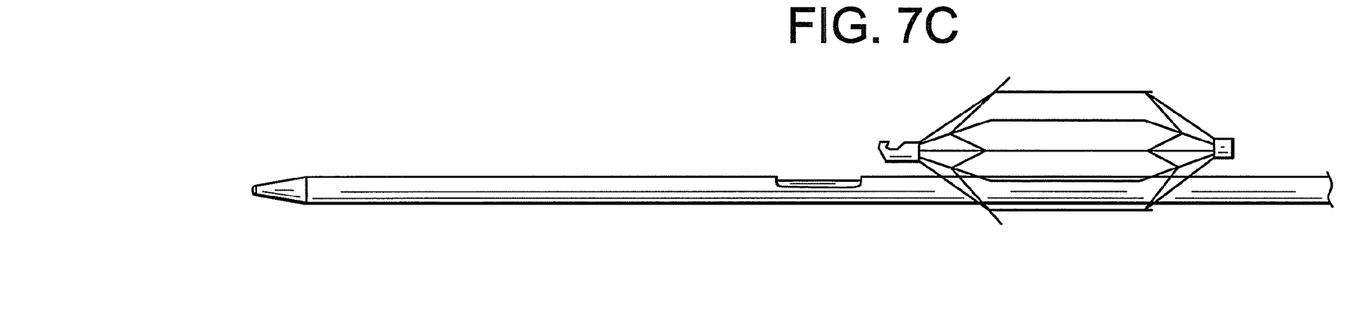

Likewise, to retrieve a filter in the distal direction, as shown in FIGS. 7A-7C, the distal end 22 of the shaft 12 is advanced to a position past the filter 46, until the sidehole 24 is aligned with the filter retrieval feature 48, which may be for example one or more hooks, barbs, loops, etc.

Figures 7D, 7E:
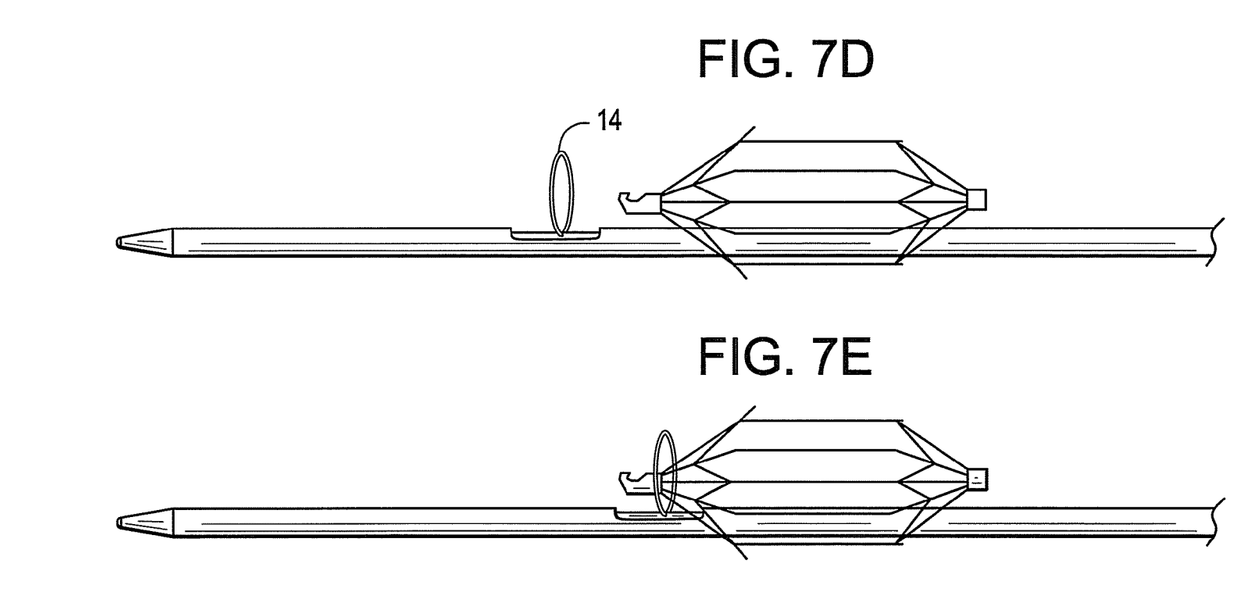
Figure 7F:
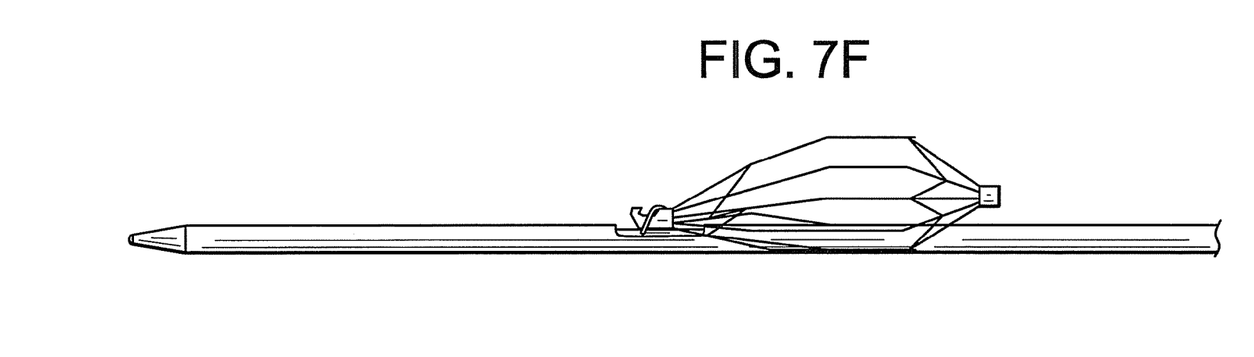
Figure 7G:
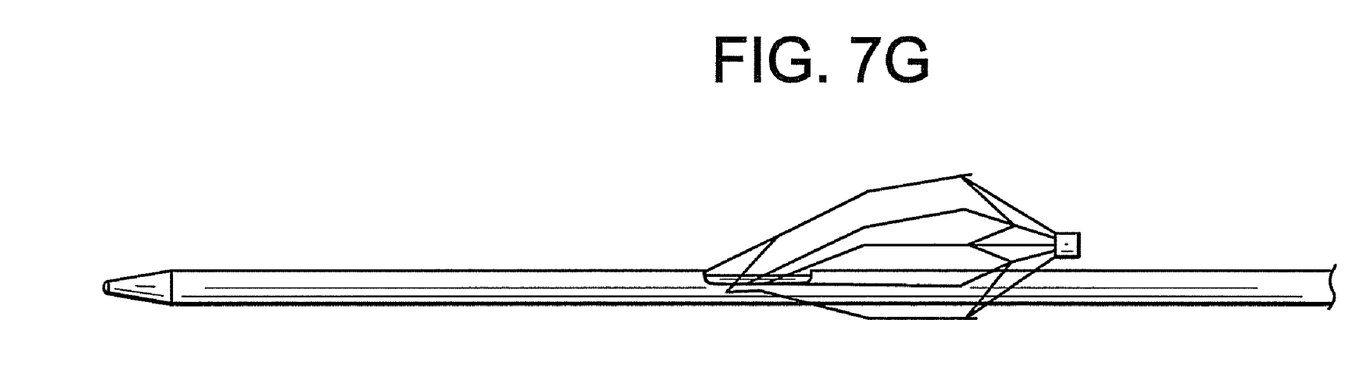
Figure 7H:
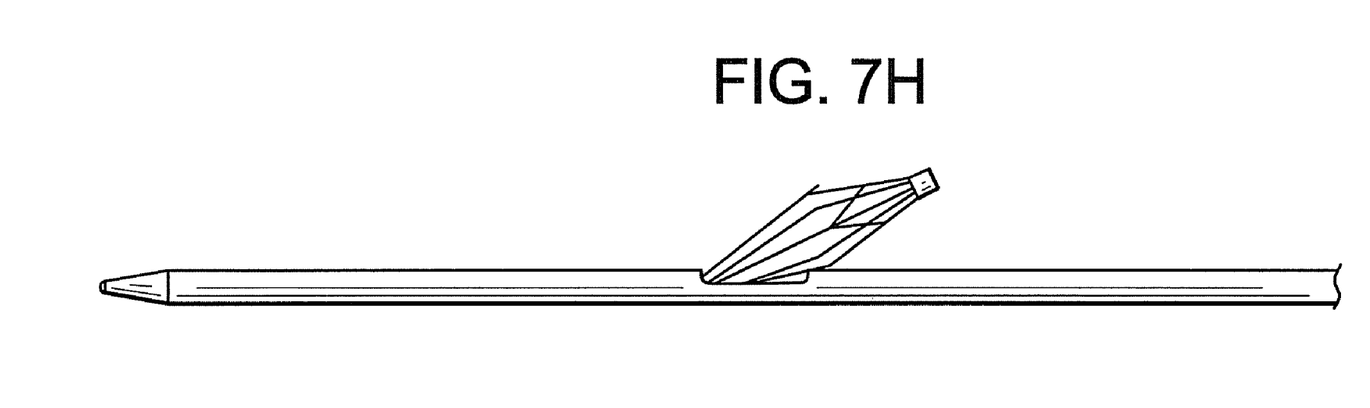
Figure 7I:
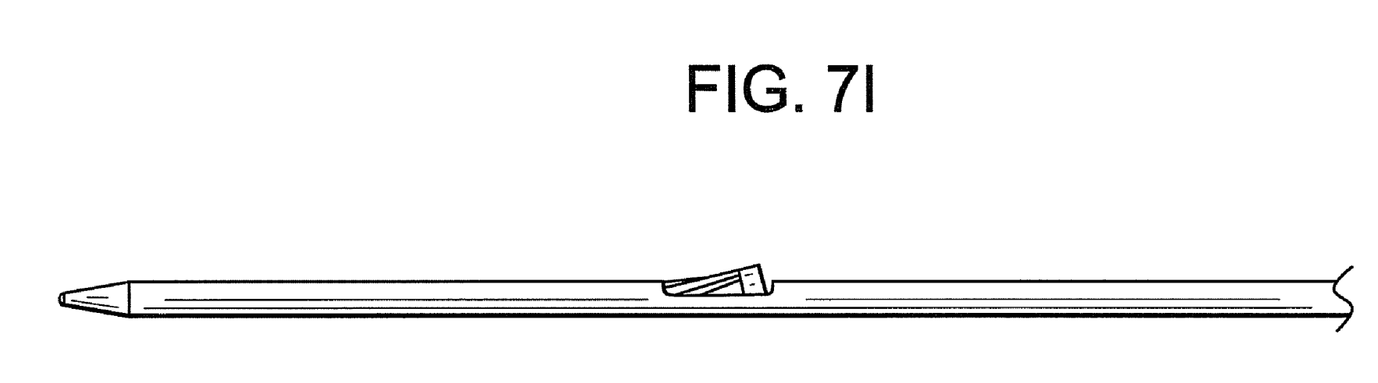
Figure 7J:
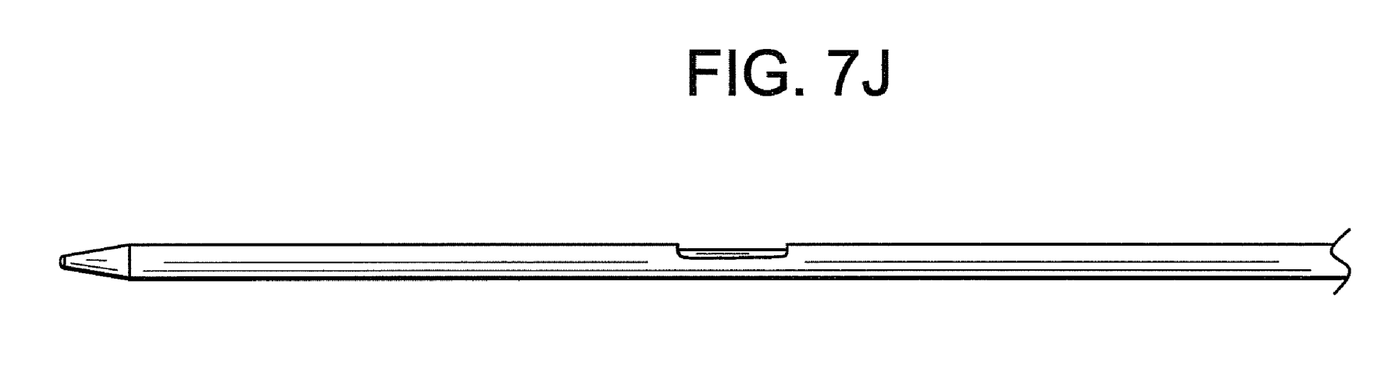

The wheel 18 is rotated slightly to move the main wire loop 38 inside the catheter shaft 12 to expose the retrieval element or snare 14, shown in FIG. 7D.

The catheter shaft is pulled or withdrawn in the proximal direction so the snare 14 moves toward the filter, so that the snare 14 surrounds the filter retrieval feature 48 or attachment point, shown in FIG. 7E.

The wheel 18 is again rotated to pull the snare 14 in the distal direction, to draw the filter 46 into the catheter shaft 12 until it is inside the distal internal space 32, shown in FIGS. 7F-7J. The retrieval system and captured filter are then removed from the body.

The components of the retrieval systems of the present invention may be made of any suitable material having the desired performance characteristics, including biocompatibility, strength, flexibility, etc. For example, in the particular retrieval system shown in the drawings, the handle and wheel may be made of metals, polymers, or even ceramics, while the shaft may be made of any suitable polymer, possibly in combination with a metal component such as a hypotube, and the retrieval element and main wire loop are preferably made of metal or a filament material.

The total length of the catheter may be selected as any appropriate length, which may be approximately 50-100 centimeters, to allow access to the desired sites for treatment from various insertion points.

Numerous arrangements of and modifications to the present invention will be readily apparent to those skilled in the art. For example, the portion of the main wire loop inside of the catheter shaft that does not have the snare attached to it may be contained inside a separate lumen of the catheter. Also, a separate guide wire lumen and a distal guidewire port may be provided in the catheter shaft to allow the retrieval system to be inserted over a guidewire. Also, the distal end of the catheter shaft may be pre-curved or shaped, and/or may be steerable by means of a separate wire or filament to improve the alignment of the retrieved filter to the opening of the catheter shaft. The actuator may be replaced with any suitable mechanism, including for example a slider. Also, instead of using a spool, two ends of the main wire used to manipulate the snare may simply pass through the handle or hub so that the physician may operate them individually. Also, the edges of the sidehole in the catheter may be flared or shaped to facilitate entry of the filter. Also, the shaft or main wire loop may be provided with radiopaque marker bands, which are visible on a fluoroscope or X-ray video screen.

In addition, the retrieval systems of the present invention may be used to retrieve any type of implantable medical device that has a suitable retrieval feature, and is radially compressible and capturable within the retrieval system.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A filter retrieval system for retrieving a previously implanted medical filter, comprising: a flexible shaft defining a longitudinal axis and having a proximal and a distal end; the shaft having an opening positioned a distance from the shaft distal end; the shaft defining a first internal space and second internal space positioned proximally and distally of the opening, respectively; a handle affixed to the shaft near the shaft proximal end; an actuator coupled to the handle; a main fiber loop coupled to the actuator, and a snare affixed to the main fiber loop, wherein the shaft further comprises a guide for the main fiber loop in an internal space distal of the opening and a portion of the main fiber loop is distal of the snare, the snare being longitudinally movable among a range of positions, including the position of the shaft opening and the positions of the first internal space and the second internal space; wherein the actuator, main fiber loop, and snare are configured such that moving the actuator to a desired position causes the main fiber loop to move the snare to a corresponding position; such that when the actuator is in an initial position, the snare is located within one of the first and second internal spaces; such that when the actuator is moved to a ready position, the snare moves from the one of the first and second internal spaces to the shaft opening and protrudes from the shaft opening; such that the snare can be maneuvered to engage a portion of a filter, and then the actuator can be moved to a first or second capture position which pulls the filter through the shaft opening into a selected one of the first and second internal spaces, wherein the guide is selected from the group of a pin, a pulley and a U- shaped channel, and a distal portion of the main fiber loop extends around the guide.

2. The filter retrieval system in accordance with claim 1, wherein a portion of the main fiber loop is distal of the second internal space.

3. The filter retrieval system in accordance with claim 1, wherein the snare defines a second loop, in addition to main fiber loop.

4. A filter retrieval system for retrieving a previously implanted medical filter, comprising: a flexible shaft defining a longitudinal axis and having a proximal and a distal end; the shaft having an opening positioned a distance from the shaft distal end; the shaft defining a first internal space and second internal space positioned proximally and distally of the opening, respectively; a handle affixed to the shaft near the shaft proximal end; an actuator coupled to the handle; a main fiber loop coupled to the actuator, and a snare affixed to the main fiber loop, the snare being longitudinally movable among a range of positions, including the position of the shaft opening and the positions of the first internal space and the second internal space; wherein the actuator, main fiber loop, and snare are configured such that moving the actuator to a desired position causes the main fiber loop to move the snare to a corresponding position; such that when the actuator is in an initial position, the snare is located within one of the first and second internal spaces; such that when the actuator is moved to a ready position, the snare moves from the one of the first and second internal spaces to the shaft opening and protrudes from the shaft opening; such that the snare can be maneuvered to engage a portion of a filter, and then the actuator can be moved to a first or second capture position which pulls the filter through the shaft opening into a selected one of the first and second internal spaces, wherein the material of the main fiber loop has substantially no column strength, such that the main fiber loop is incapable of transmitting an effective pushing force from the actuator to the snare.

* * * * *